US00PP34546P2

(12) United States Plant Patent
Couturieux

(10) Patent No.: US PP34,546 P2
(45) Date of Patent: Sep. 6, 2022

(54) ***HYDRANGEA* PLANT NAMED 'COUSTAR02'**

(50) Latin Name: *Hydrangea paniculata*
Varietal Denomination: COUSTAR02

(71) Applicant: Jacques Couturieux, Moyenmoutier (FR)

(72) Inventor: Jacques Couturieux, Moyenmoutier (FR)

( * ) Notice: Subject to any disclaimer, the term of this patent is extended or adjusted under 35 U.S.C. 154(b) by 0 days.

(21) Appl. No.: 17/529,826

(22) Filed: Nov. 18, 2021

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
CPC ..... A01H 6/48; A01H 5/02
See application file for complete search history.

*Primary Examiner* — Keith O. Robinson
(74) *Attorney, Agent, or Firm* — Weatherly IP Solutions, LLC; James M. Weatherly

(57) ABSTRACT

A new *Hydrangea* plant named 'COUSTAR02' particularly distinguished by having compact habit; and an inflorescence color changing from white to pink to dark red, is disclosed.

3 Drawing Sheets

Genus and species: *Hydrangea paniculata.*
Variety denomination: 'COUSTAR02'.

BACKGROUND OF THE NEW PLANT

The present invention comprises a new and distinct variety of *Hydrangea* plant, botanically known as *Hydrangea paniculata*, and hereinafter referred to by the variety name 'COUSTAR02'. 'COUSTAR02' originated from an open pollination in Moyenmoutier, France in March 2011 using an unknown female *Hydrangea paniculata* parent and an unknown male *Hydrangea paniculata* parent. Seeds from the open-pollination were taken from the female parent and sown and a single plant was chosen in 2013.

'COUSTAR02' was first propagated in June 2015 in France. 'COUSTAR02' was found to reproduce true to type in successive generations of asexual propagation via softwood cuttings.

SUMMARY

The following are the most outstanding and distinguishing characteristics of this new variety when grown under normal horticultural practices in Boskoop, The Netherlands.

1. Compact habit; and
2. Inflorescence color changing from white to pink to dark red.

DESCRIPTION OF THE PHOTOGRAPHS

This new *Hydrangea* plant is illustrated by the accompanying photographs which shows the plant's overall plant habit including form, and foliage. The photographs are of a two year old plant from cuttings grown in a 17-cm container. Photos were taken in August 2021 in Boskoop, The Netherlands. The colors shown are as true as can be reasonably obtained by conventional photographic procedures.

Figure 1:
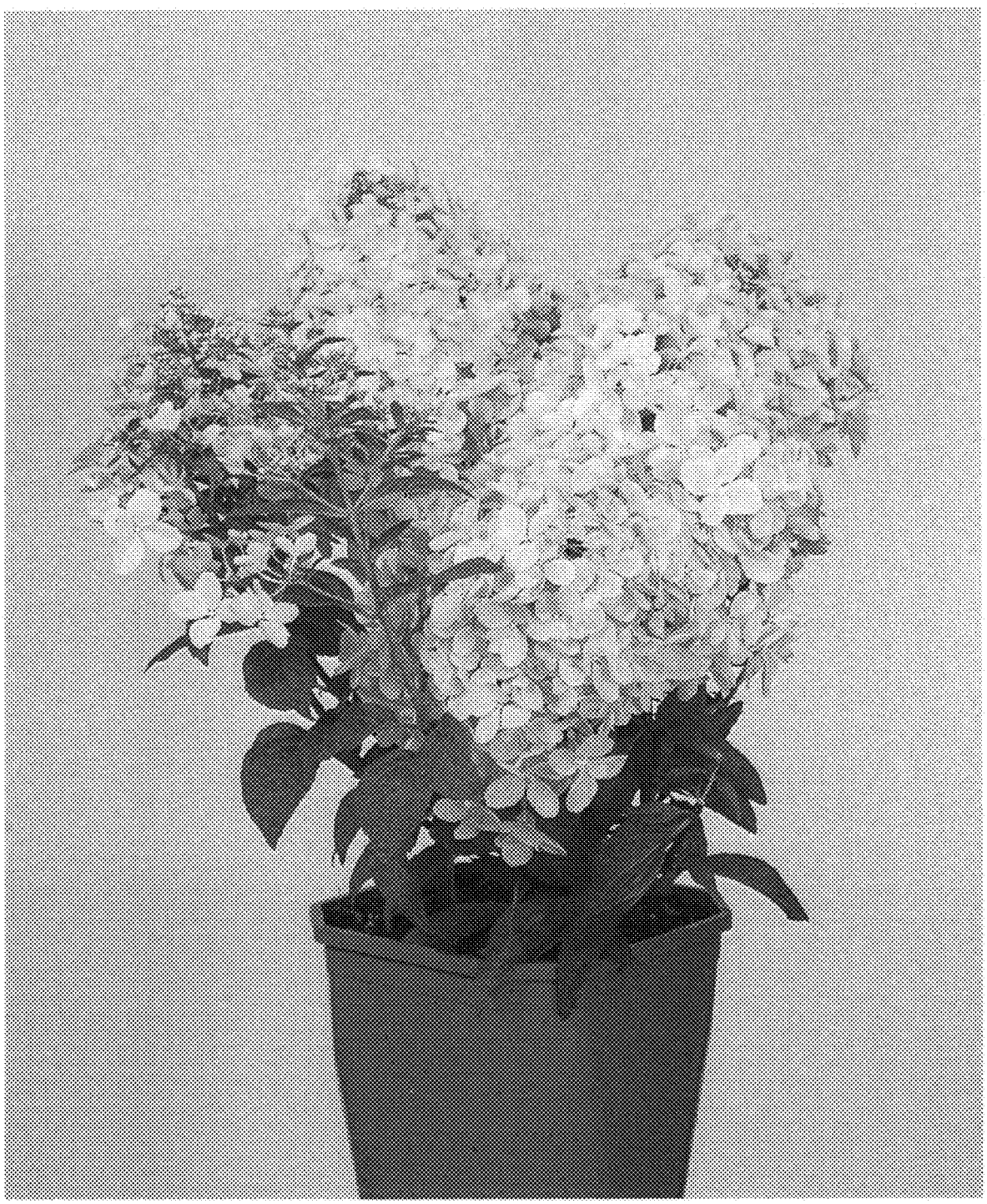
Figure 2:
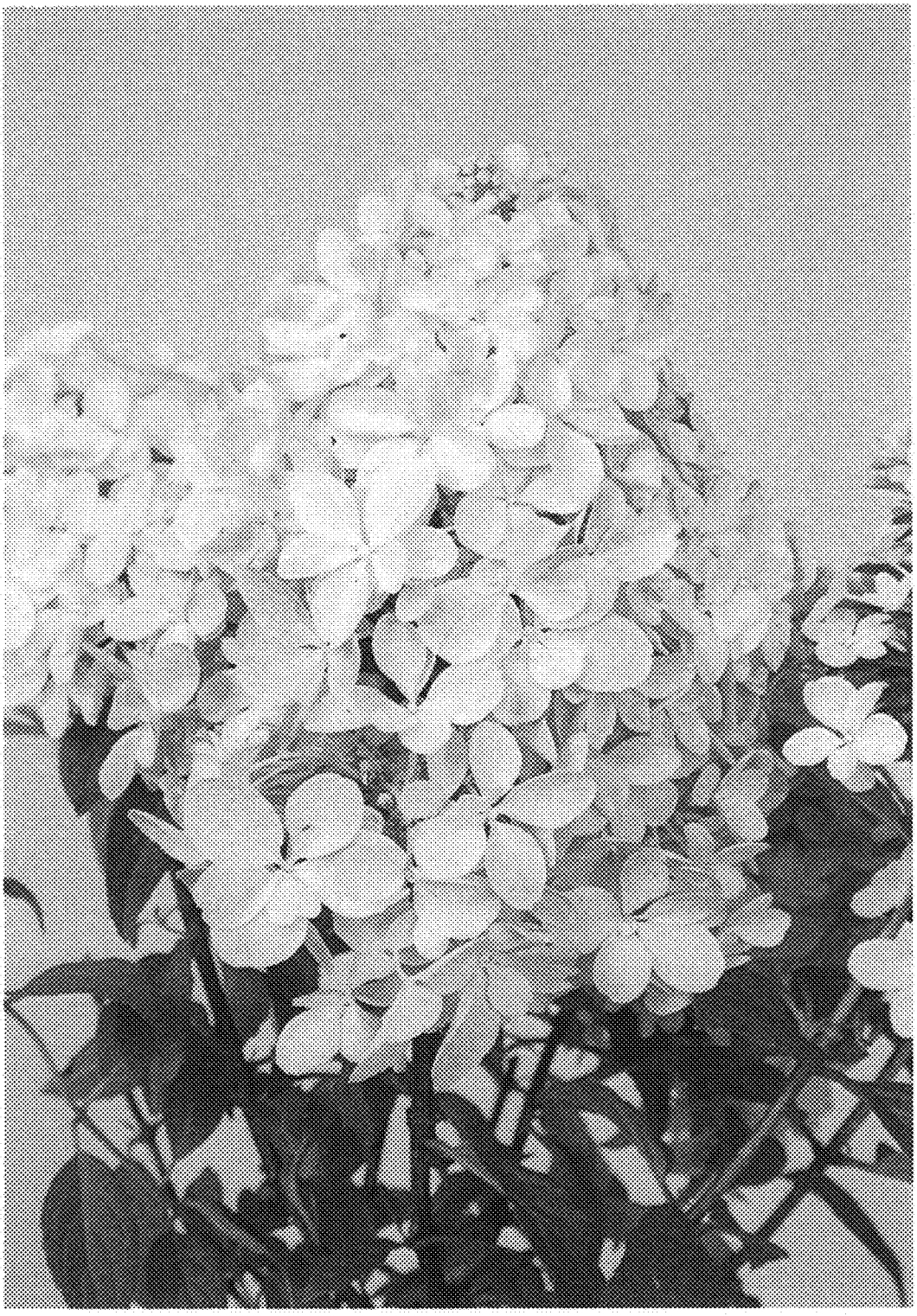
Figure 3:
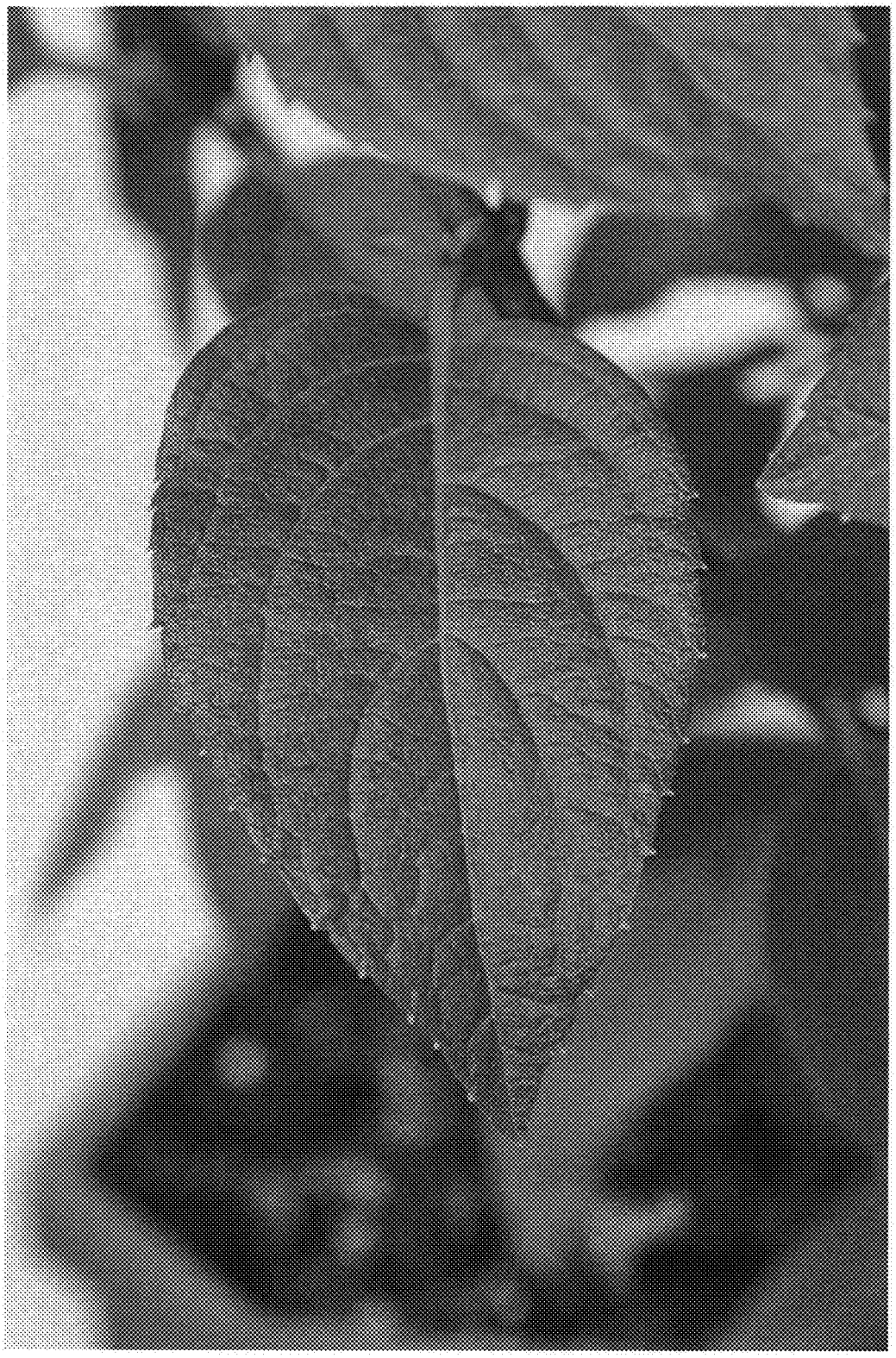

FIG. 1 shows the overall plant habit of 'COUSTAR02'.
FIG. 2 shows a close-up of the flowers.
FIG. 3 shows a close-up of the foliage.

DESCRIPTION OF THE NEW VARIETY

The following detailed descriptions set forth the distinctive characteristics of 'COUSTAR02'. The data which define these characteristics were collected from asexual reproductions carried out in Boskoop, The Netherlands. Data was collected on two-year old plants grown outdoors in 17 cm square containers in Boskoop, The Netherlands in August 2021. The range of day temperatures was 16° C. to 26° C. and the range of night temperatures was 8° C. to 20° C. Color references are to The R.H.S. Colour Chart of The Royal Horticultural Society of London (R.H.S.), 6$^{th}$ edition (2015).

Classification:
- *Family.*—Hydrangeaceae.
- *Botanical.*—*Hydrangea paniculata.*
- *Common.*—*Hydrangea.*
- *Designation.*—'COUSTAR02'.

Plant:
- *Propagation type.*—Vegetative cuttings.
- *Time to produce a finished plant.*—Average is twelve months from propagation to a small, finished plant.
- *Appropriate for what size of container.*—Field grown and in 13 in pots or larger.
- *Plant shape.*—Short ovate.
- *Average plant height.*—39.5 cm.
- *Average plant diameter.*—39.2 cm.
- *Growth habit.*—Broad spreading-upright.
- *Growth rate.*—Low to moderate.
- *Vigor.*—Moderate.
- *Heat tolerance.*—At least tolerant to USDA Zone 9.
- *Cold tolerance.*—Tolerant to USDA Zone 5.
- *Tolerance to wind.*—Moderate.
- *Tolerance to rain.*—Moderate to high.

Branches:
- *Habit.*—Freely branching.
- *Basal branching.*—Present.

*Pinching*.—Not required but will improve branching.

*Lateral branches*.—Number of lateral branches per plant: Average of 10. Length: Average is 17.6 cm, excluding inflorescence. Diameter: Average is 0.5 cm. Internode length: Average is 4.5 cm. Appearance and shape: Rounded. Aspect/angle: Upright; average angle of 60 degrees to main branch. Strength: Strong. Color, immature: RHS 146D (Yellow-green). Color, mature: RHS 199A (Grey-brown) and RHS 199B (Grey-brown); Older bark and RHS 197B to RHS 197D (Greyed-green) and RHS 199A, RHS N199A and RHS N199B (Grey-brown). Pubescence: Young stems sparsely to moderately covered with short adpressed hairs, average length: 0.5 mm, colored green-white; too small and too sparsely present to be measured with RHS-CC. Lenticels: Stems sparsely to moderately covered with lenticels, average length 1.5 mm, average width 0.75 mm, colored RHS 164B (Greyed-orange); lenticels not visible on mature stems.

Foliage:

*Arrangement*.—Opposite or in whorls of three.

*Shape*.—Ovate.

*Apex*.—Apiculate to acute.

*Base*.—Acute to short attenuate.

*Margin*.—Serrate.

*Length*.—Average is 6.9 cm.

*Width*.—Average is 3.7 cm.

*Texture*.—Upper and lower surfaces: Smooth, moderately pubescent.

*Pubescence*.—Both sides moderately pubescent with very short strigose hairs, adpressed on underside of lamina, on upper side average length: 0.3 mm, colored greyed-white; too small and too sparsely present to be measured with RHS-CC, on under side average length: 0.4 mm, colored green-white; too small and too sparsely present to be measured with RHS-CC.

*Venation pattern*.—Pinnate.

*Venation color*.—Upper surface: RHS 144A (Yellow-green). Lower surface: RHS 147C (Yellow-green).

*Color*.—Immature: Upper surface: RHS 143A to RHS 144A (Green to Yellow-green). Lower surface: RHS 146B (Yellow-green). Mature: Upper surface: RHS 137A (Green). Lower surface: RHS 146B (Yellow-green).

*Petiole*.—Length: Average 0.9 cm. Diameter: Average is 2.5 mm. Color: Upper surface: RHS 146B to RHS 146C (Yellow-green), with RHS 174A margins (Greyed-orange). Lower surface: RHS 146C to RHS 146D (Yellow-green), with RHS 174A margins (Greyed-orange). Texture: Upper surface: Slightly glossy, margins sparsely covered with very short strigose hairs, average length: 0.3 mm, colored white; too small and too sparsely present to be measured with RHS-CC. Lower surface: Slightly glossy, sparsely covered with very short strigose hairs, average length: 0.3 mm, colored white; too small and too sparsely present to be measured with RHS-CC.

Flowers:

*Natural flowering season*.—Mid-summer to late summer.

*Time to flower*.—One season.

*Fragrance*.—Very faint, sweet and pleasant, typical H. paniculata-scent.

*Inflorescence type*.—Paniculate.

*Conspicuousness of the fertile flowers of the inflorescence*.—Medium.

*Panicle*.—Shape: Irregular, broad conical. Height: 19.3 cm. Diameter: 18.9 cm.

*Peduncle*.—Length: 18.7 cm. Diameter: 0.4 cm. Angle: Main peduncle straight on top of lateral branch (=0°), lateral peduncles in an average angle of 52.5° to main peduncle. Strength Moderately strong. Texture: Matte, densely covered with thin adpressed hairs; average length of hairs 0.4 mm, RHS 157D (Green-white). Color: RHS 148D (Yellow-green); sparsely to moderately covered with lenticels, average length: 1.0 mm, average diameter: 0.5 mm, colored RHS 157A (Green-white).

*Sterile florets bud*.—Average length: 0.9 cm. Average diameter: 1.0 cm. Shape: Cup-shaped. Color: RHS 150C (Yellow-green).

*Fertile florets bud*.—Average length: 0.40 cm. Average diameter: 0.40 cm. Shape: Broad ovate. Color: RHS 157B (Green-white) top tinged RHS 62C (Red-purple) base (immature calyx) RHS 145C (Yellow-green).

*Sterile florets*.—Persistent with an average of 475 of sterile florets per inflorescence. Aspect: Upright and outward to slightly drooping. Shape: Rotate. Average diameter: 4.4 cm. Average depth: 0.6 cm. Longevity of florets on plant is 6 weeks. Petals: Number per floret: 4, occasionally 3 or 5. Arrangement: Rotate. Shape: Ovate. Tip: Acute. Base: Cuneate. Margin: Entire. Length: 0.3 cm. Width: 0.15 cm. Texture: Upper surface: Smooth, glabrous and very slightly glossy. Lower surface: Smooth, glabrous and matte. Color when opening: Upper surface: RHS 157A (Green-white) fading lighter to the margins of RHS 157D. Lower surface: RHS 145D (Yellow-green), tipped RHS 62B (Red-purple). Color full open: Upper surface: RHS 157B (Green-white) fading lighter to the margins of RHS 157D. Lower surface: RHS 157A (Green-white).

*Sepals*.—Average number: 4 or 5 per floret. Arrangement: Rotate. Shape: Obovate to broad elliptic. Apex: Shallowly retuse to obtuse. Base: Narrowly cuneate. Margin: Entire, occasionally shallowly toothed on upper half. Length: 2.4 cm. Width: 1.8 cm. Texture (both surfaces): Glabrous and matte. Color: When opening: Upper surface: A blend of RHS 145D (Yellow-green) and RHS 150D (Yellow-green). Lower surface: Slightly lighter then RHS 145D (Yellow-green), fading to slightly lighter than RHS 150D toward the top. Fully opened: Upper surface: RHS 145B (Yellow-green) and RHS 145C (Yellow-green). Lower surface: RHS 145C (Yellow-green). Fading to: Upper surface: RHS 68C (Red-purple). Lower surface: RHS 63B (Red-purple) to RHS 63C (Red-purple).

*Pedicel*.—Length: 2.5 cm. Diameter: 0.1 cm. Angle: 40 degrees to main peduncle. Strength: Moderately strong. Texture: Matte, very sparsely covered with thin adpressed hairs, average length of hairs is shorter than 0.04 cm. Color: RHS 157C (Green-white), fading to RHS 145D (Yellow-green) at proximal end.

Fertile flowers:

*Number of fertile flowers per inflorescence.*—500.

*Aspect.*—Upright.

*Shape.*—Rotate, petals drop when maturing.

*Diameter.*—0.75 cm.

*Depth.*—0.5 cm.

*Flower longevity.*—Five days.

*Persistent or self-cleaning.*—Self-cleaning.

*Petals.*—Petals per flower: 5. Arrangement: Rotate. Shape: Ovate, moderately concave. Tip: Acute. Base: Cuneate. Margin: Entire. Length: 0.3 cm. Width: 0.15 cm. Texture: Upper surface: Smooth, glabrous, very slightly glossy. Lower surface: Smooth, glabrous matte. Color when opening: Upper surface: RHS 157A (Green-white), fading lighter toward RHS 157D margins. Lower surface: RHS 145D (Yellow-green), tipped RHS 62B (Red-purple). Color fully open: Upper surface: RHS 157B (Green-white), fading lighter RHS 157D toward the margins. Lower surface: RHS 157A (Green-white).

*Sepals.*—Number: 5. Arrangement: Rotate. Shape: Deltoid. Tip: Broad acuminate. Base: Broad cuneate. Margin: Entire. Length: 0.15 cm. Width: 0.12 cm. Texture: Both surfaces: Glabrous matte. Color when opening: Upper surface: RHS 145D (Yellow-green). Lower surface: RHS 145C (Yellow-green). Color fully open: Upper surface: RHS 145D (Yellow-green). Lower surface: RHS 145C to RHS 145D (Yellow-green).

*Pedicel.*—Length: 0.2 cm. Diameter: 0.05 cm. Angle: 20 degrees to main peduncle. Strength: Moderate. Texture: Matte, moderately to densely covered with a thin pubescence; average length of hairs: 0.3 mm, colored white to green-white; too small and too sparsely present to be measured with RHS-CC. Color: RHS 145C to RHS 145D (Yellow-green).

Reproductive organs:

*Sterile flowers.*—Androecium: Present. Stamens: 8. Filament length: 0.2 cm. Filament color: RHS NN155A (White). Anther shape: Broad oblong. Anther length: 0.075 cm. Anther color: RHS 157A (Green-white). Pollen amount: Low to moderate. Pollen color: RHS 156D (Greyed-white). Gynoecium: Present. Pistils per floret: 2. Pistil length: 0.2 cm. Stigma shape: Club-shaped. Stigma color: RHS 145C (Yellow-green). Style length: 0.125 cm. Style color: RHS 145D (Yellow-green). Ovary: Not present.

*Fertile flowers.*—Stamens: 10. Filament length: 0.25 cm. Filament color: RHS NN155B (White). Anther shape: Broad oblong. Anther length: 0.075 cm. Anther color: is RHS 157A (Green-white) and slightly darker. Pollen amount: Low to moderate. Pollen color: RHS 156D (Greyed-white). Pistils: 3. Pistil length: 0.2 cm. Stigma shape: Club-shaped. Stigma color: RHS 145C to RHS 145D (Yellow-green). Style length: 0.1 cm. Style color: RHS 145D (Yellow-green). Ovary color: RHS 145D (Yellow-green).

Seed: Not observed.

Disease and pest resistance: The disease which are occur in *H. paniculata* and also in COUSTAR02 are: white fly, black spots, powdering mildew, lice.

COMPARISON WITH PARENTAL LINES

The parental lines for 'COUSTAR02' are unknown so no comparison information is available.

COMPARISON TO KNOWN VARIETY

'COUSTAR02' is most similar to the commercial *Hydrangea* plant named 'ILVOBO' (U.S. Plant Pat. No. 22,782). Differences between the two varieties are described in Table 1:

TABLE 1

Comparison with Similar Variety

| Characteristic | Variety 'COUSTAR02' | Commercial line 'ILVOBO' |
|---|---|---|
| Fertile petals (fully open) | Upper surface: RHS 157B (Green-white), fading lighter RHS 157D toward the margins Lower surface: RHS 157A (Green-white) | Fully opened, upper and lower surfaces: Close to 155C. |
| Fertile floret bud | Color: RHS 157B (Green-white) top tinged RHS 62C (Red-purple) base (immature calyx) RHS 145C (Yellow-green) | Close to 155C |
| Pedicel color | RHS 145C to RHS 145D | Close to RHS 155A |

I claim:

1. A new and distinct cultivar of *Hydrangea* Plant Named 'COUSTAR02' as described and illustrated herein.

* * * * *